(12) United States Patent
Stefinovic et al.

(10) Patent No.: US 9,145,400 B2
(45) Date of Patent: Sep. 29, 2015

(54) PROCESS FOR THE PREPARATION OF FORM III OF VILAZODONE HYDROCHLORIDE

(71) Applicant: Sandoz AG, Basel (CH)

(72) Inventors: Marijan Stefinovic, Kundl (AT); Clemens Haefele, Innsbruck (AT); Ulrich J. Griesser, Innsbruck (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/326,921

(22) Filed: Jul. 9, 2014

(65) Prior Publication Data

US 2015/0018370 A1    Jan. 15, 2015

(30) Foreign Application Priority Data

Jul. 12, 2013    (EP) ..................... 13176400

(51) Int. Cl.
*C07D 405/12*    (2006.01)
(52) U.S. Cl.
CPC .................. *C07D 405/12* (2013.01)

(58) Field of Classification Search
CPC ................................................... C07D 405/12
See application file for complete search history.

(56) References Cited

U.S. PATENT DOCUMENTS 5,532,241 A    7/1996    Boettcher

FOREIGN PATENT DOCUMENTS

WO    02/102794 A2    12/2002
WO    2012/131706 A1    10/2012

OTHER PUBLICATIONS

Search Report issued in European Patent Application No. 13176400.3-1452 on Sep. 30, 2013, pp. 1-8.
Sorbera, Vilazodone Hydrochloride:, Drugs of the Future, Prous Science, ES, vol. 26, No. 3, Jan. 1, 2001, pp. 247-252.

*Primary Examiner* — Brian McDowell
(74) *Attorney, Agent, or Firm* — Jeffrey S. Melcher; Manelli Selter PLLC

(57) ABSTRACT

The invention relates to a new solvate, Vilazodone hydrochloride monoethanol monohydrate solvate, and to a process for the preparation of polymorphic form III of Vilazodone hydrochloride via the Vilazodone hydrochloride monoethanol monohydrate solvate.

8 Claims, 1 Drawing Sheet

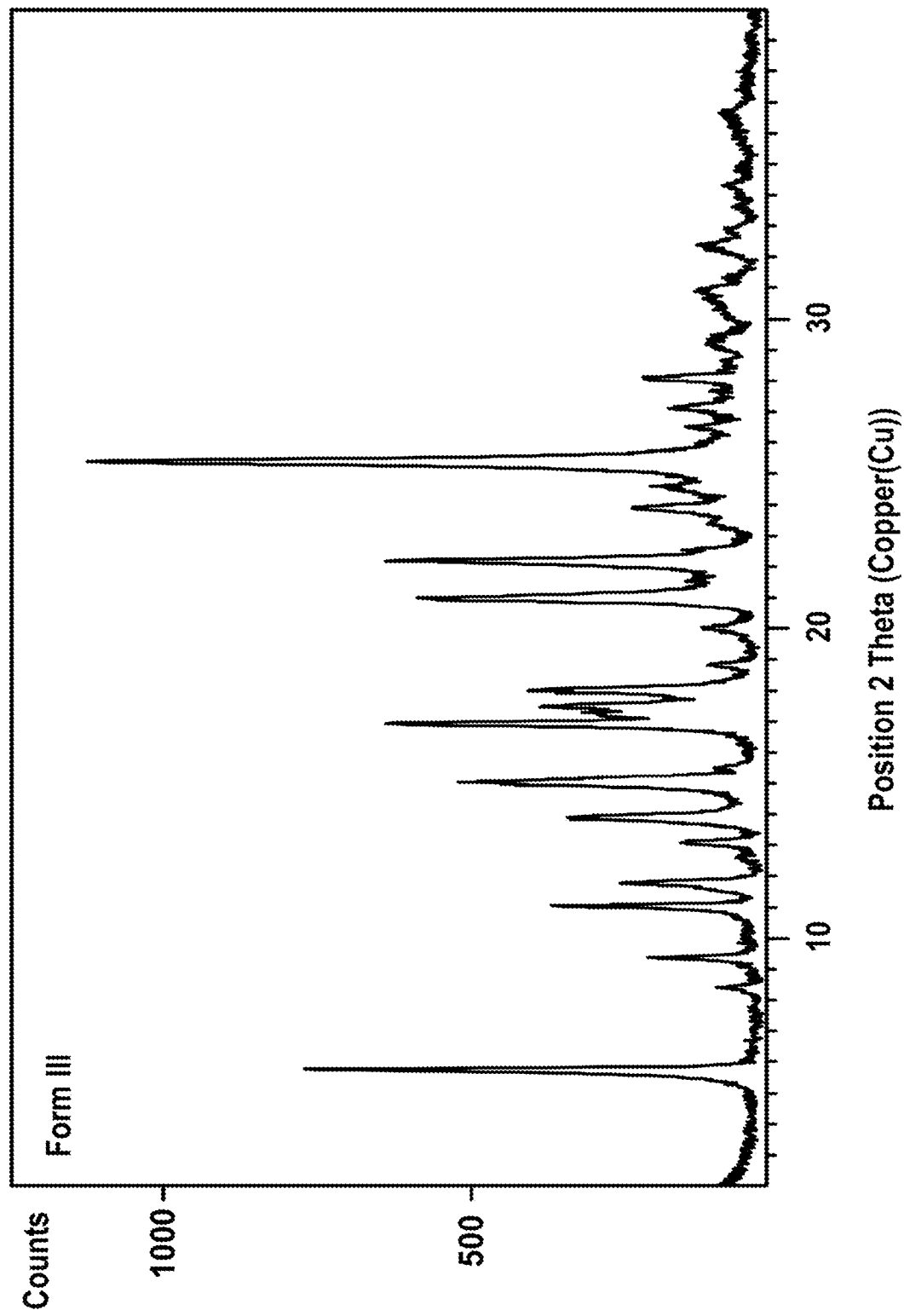

PROCESS FOR THE PREPARATION OF FORM III OF VILAZODONE HYDROCHLORIDE

This application claims priority to European Patent Application No. EP13176400.3 filed 12 Jul. 2013, the complete disclosure of which is incorporated herein by reference.

FIELD OF THE INVENTION

The present invention is directed to a process for the preparation of polymorphic form III of vilazodone hydrochloride via a novel solvate of vilazodone hydrochloride.

BACKGROUND ART

Vilazodone hydrochloride, IUPAC name 5-(4-[4-(5-cyano-1H-indol-3-yl)butyl]piperazin-1-yl)benzofuran-2-carboxamide hydrochloride, physiologically acceptable salts thereof and their use in treating certain medical disorders are known from U.S. Pat. No. 5,532,241 and WO 00/72832. Polymorphic forms of Vilazodone hydrochloride are disclosed in WO 02/102794.

Vilazodone was approved by the FDA for the treatment of major depressive disorders on Jan. 21, 2011. It is being marketed under the trade name Viibryd.

WO 02/102794 describes that form III of Vilazodone hydrochloride is the most thermodynamically stable polymorph of Vilazodone hydrochloride at room temperature (see WO 02/102794 page 20, lines 23-26 and FIG. 27). In addition WO 02/10274 describes that form III of Vilazodone hydrochloride is non-hygroscopic, e.g. it takes up water only in minimal amounts when exposed to a humidity of about 90% as shown by DVS (dynamic vapor sorption).

However, the process for the preparation of form III disclosed in WO 02/102794 has serious drawbacks. It comprises dispersing Vilazodone free base in tetrahydrofuran, converting the free base to the hydrochloride by the addition of hydrochloric acid, precipitation of form II (a solvate with tetrahydrofuran) and drying of the obtained tetrahydrofuran solvate at a temperature of at least 100° C. to yield form III.

Tetrahydrofuran is a class 2 solvent with a PDE of 7.2 mg/day and a limit of 720 ppm (see ICH Toxic Q3C (M) Maintenance of Note for Guidance on Impurities: Residual solvents (CPMP/ICH/283/95)). 720 ppm is a limit very difficult to achieve by drying Vilazodone hydrochloride tetrahydrofuran solvate, which releases tetrahydrofuran only under quite harsh conditions.

Thus the disadvantages of the described processes for the preparation of form III of Vilazodone hydrochloride are in contrast with the on the other hand described favorable properties of form III.

SUMMARY OF THE INVENTION

The invention relates to a novel process for the preparation of form III of Vilazodone hydrochloride.

A novel solvate of Vilazodone hydrochloride, namely Vilazodone hydrochloride monoethanol monohydrate solvate has been found as a useful intermediate for form III production.

The novel process for the preparation of Vilazodone hydrochloride comprises the desolvation of Vilazodone hydrochloride monoethanol monohydrate solvate to form III of Vilazodone hydrochloride.

BRIEF DESCRIPTION OF THE DRAWING

FIG. 1 illustrates an PXRD of Vilazodone hydrochloride form III

Crystal structure analysis: Intensity data for the crystal structure analysis were collected with Cu (l=1.5418 Å) radiation on an Oxford Diffraction Gemini-R Ultra diffractometer, which was operated by the CrysAlis software. The structure was solved using the direct methods procedure in SHELXS97 and refined by full-matrix least squares on $F^2$ using SHELXL97. All non-hydrogen atoms were refined anisotropically.

X-ray powder diffraction: X-ray powder diffraction patterns (PXRD) were obtained with a X'Pert PRO diffractometer (PANalytical, Almelo, The Netherlands) equipped with a theta/theta coupled goniometer in transmission geometry, programmable XYZ stage with well plate holder, Cu-K$\alpha$1, 2 radiation source (wavelength 0.15419 nm) with a focusing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The patterns were recorded at a tube voltage of 40 kV, tube current of 40 mA, applying a step size of 0.013° 2 theta with 80 s per step in the angular range of 2° to 40° 2 theta.

DETAILED DESCRIPTION OF THE INVENTION

The present invention relates to a new solvate of Vilazodone hydrochloride, namely Vilazodone hydrochloride monoethanol monohydrate solvate. It has been found that this solvate unexpectedly allows production of a Vilazodone form III with advantageous properties.

Vilazodone hydrochloride monoethanol monohydrate solvate is crystalline and has as an advantage that it allows for an easy desolvation process to yield Vilazodone hydrochloride form III. Moreover, only water and ethanol, harmless class 3 solvents, are present in small amounts in the Vilazodone hydrochloride form III obtained from and by the process of the invention.

Vilazodone hydrochloride crystalline form III may be characterized by a x-ray powder diffraction pattern (XRPD) comprising at least 5 peaks, preferably at least 8 peaks at 2$\theta$ values selected from the group consisting of 5.82, 11.00, 14.89, 16.96, 17.41, 17.97, 21.16, 22.05, 25.28, 28.03 when measured at a temperature of about 20° C. and an x-ray wavelength (CuK$\alpha$)$\lambda$, of 1.5418 Å. It has been described to be the thermodynamically most stable form of Vilazodone hydrochloride at room temperature (see WO 02/102794 page 20, lines 23-26 and FIG. 27).

Vilazodone hydrochloride monoethanol monohydrate solvate—chemical formula $C_{26}H_{27}N_5O_2 \times HCl \times C_2H_6O \times H_2O$—can be characterized by X-ray structural analysis as having a triclinic cell belonging to space group P-1, with unit cell dimensions of a [Å]=7.08707, b [Å]=10.7069, c [Å]=16.9149, alpha [°]=84.930, beta [°]=82.535, gamma [°]=85.286, a cell volume [Å$^3$] of about 1404.18 and Z (formula units per elementary cell)=2.

The atomic coordinates of Vilazodone hydrochloride monoethanol monohydrate solvate described in table 1 were determined using the above method for crystal structure analysis.

TABLE 1 atomic coordinates of Vilazodone hydrochloride monoethanol monohydrate

| atom | x | y | z | U | atom | x | y | Z | U |
|---|---|---|---|---|---|---|---|---|---|
| Cl(1) | 0.51498(7) | 0.58749(5) | 0.24208(3) | 0.03949(19) | C19 | −0.0688(3) | 1.2677(2) | 0.30981(14) | 0.0345(5) |
| O(1) | −0.37779(18) | 2.04011(13) | −0.63750(9) | 0.0314(3) | C20 | 0.0019(3) | 1.2725(2) | 0.23113(14) | 0.0373(5) |
| C(2) | −0.3170(3) | 2.12755(19) | −0.59533(14) | 0.0323(5) | C21 | 0.0724(3) | 1.1421(2) | 0.20107(14) | 0.0357(5) |
| C(3) | −0.2506(3) | 2.07330(19) | −0.52973(14) | 0.0338(5) | C22 | 0.1304(3) | 1.1419(2) | 0.11896(14) | 0.0384(5) |
| C(4) | −0.2694(3) | 1.9405(2) | −0.52847(13) | 0.0309(4) | C23 | 0.2026(3) | 1.0165(2) | 0.08703(14) | 0.0355(5) |
| C5 | −0.3482(3) | 1.92636(19) | −0.59564(13) | 0.0293(4) | C24 | 0.2317(3) | 0.9072(2) | 0.12348(15) | 0.0447(6) |
| C6 | −0.3837(3) | 1.8104(2) | −0.61675(13) | 0.0312(4) | N25 | 0.3011(3) | 0.81331(19) | 0.07303(13) | 0.0478(5) |
| C7 | −0.3373(3) | 1.70643(19) | −0.56735(13) | 0.0302(4) | C26 | 0.3186(3) | 0.8610(2) | 0.00336(14) | 0.0377(5) |
| C8 | −0.2582(2) | 1.71645(19) | −0.49786(13) | 0.0289(4) | C27 | 0.2582(3) | 0.9892(2) | 0.00920(13) | 0.0340(5) |
| C9 | −0.2274(3) | 1.8348(2) | −0.47758(13) | 0.0321(5) | C28 | 0.2626(3) | 1.0609(2) | 0.05439(14) | 0.0371(5) |
| C10 | −0.3289(3) | 2.2604(2) | −0.62746(14) | 0.0329(5) | C29 | 0.3273(3) | 1.0038(2) | 0.12273(14) | 0.0400(5) |
| O11 | −0.2656(2) | 2.33973(14) | −0.59405(10) | 0.0405(4) | C30 | 0.3876(3) | 0.8759(2) | 0.12761(14) | 0.0409(5) |
| N12 | −0.2017(2) | 1.60502(16) | −0.45414(11) | 0.0306(4) | C31 | 0.3837(3) | 0.8040(2) | 0.06547(15) | 0.0416(5) |
| C13 | −0.1357(3) | 1.6193(2) | −0.37889(13) | 0.0328(5) | C32 | 0.3305(4) | 1.0762(3) | 0.19003(17) | 0.0506(6) |
| C14 | −0.0408(3) | 1.4982(2) | −0.34977(14) | 0.0340(5) | N33 | 0.3303(4) | 1.1323(3) | 0.24432(17) | 0.0705(8) |
| N15 | −0.1546(2) | 1.39079(16) | −0.33942(11) | 0.0303(4) | O1W | 0.5853(7) | 0.4463(3) | 0.0903(2) | 0.154(2) |
| C16 | −0.2179(3) | 1.37884(19) | −0.41770(13) | 0.0321(5) | O1S | 0.2855(6) | 0.4076(4) | 0.0489(3) | 0.1337(15) |
| C17 | −0.3128(3) | 1.49995(19) | −0.44556(13) | 0.0305(4) | C1S | 0.0164(10) | 0.3848(8) | 0.1343(6) | 0.192(4) |
| N18 | −0.4081(3) | 2.28608(18) | −0.69249(12) | 0.0390(5) | C2S | 0.1641(11) | 0.4503(9) | 0.1076(6) | 0.222(6) |

The numbering system of Vilazodone hydrochloride monoethanol monohydrate solvate is shown below:

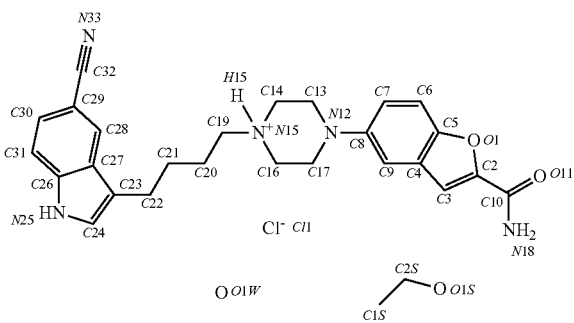

Seed crystals of the novel solvate, Vilazodone hydrochloride monoethanol monohydrate solvate, can be obtained by suspending the known form III of Vilazodone hydrochloride in 96% ethanol—96% ethanol/4% water, to be specific—and stirring the suspension for an extended period of time, for example 20 hours as described in example 1, at ambient temperature. Seed crystals can then be isolated from the suspension by simple filtration (suction).

In another embodiment, the invention relates to a process for the manufacture of Vilazodone hydrochloride monoethanol monohydrate, comprising the steps of
  (a) providing a solution of 5-4-[4-5-cyano-1H-indol-3-yl)butyl]piperazin-1yl)benzofuran-2-carboxamide hydrochloride (vilazodone hydrochloride) in a water-ethanol mixture,
  (b) precipitating Vilazodone hydrochloride monoethanol monohydrate solvate in the presence of seed crystals,
  (c) optionally diluting the suspension, preferably with ethanol or a water/ethanol mixture,
  (d) recovering Vilazodone hydrochloride monoethanol monohydrate solvate from the suspension.

Any form of Vilazodone hydrochloride or any solvate of Vilazodone hydrochloride or an amorphous form of Vilazodone hydrochloride may be used as the starting material for step a). Also a solution of Vilazodone hydrochloride prepared from Vilazodone free base and hydrochloric acid may be provided as the starting solution for crystallization of Vilazodone hydrochloride monoethanol monohydrate solvate.

The water/ethanol mixture which is to be used for preparing the solution of step a) is not particularly limited as long as a sufficient amount of water is present so as to allow formation of the hydrate and as long as enough ethanol is present so as to allow formation of the monoethanol solvate. The water/ethanol mixture can comprise 2-8% v/v water. The water/ethanol mixture can comprise at least 70% ethanol, such as 80% or 90% ethanol. Preferred water/ethanol mixtures consist of water and ethanol, for example 98% ethanol/2% water, 97% ethanol/3% water, 96% ethanol/4% water, 95% ethanol/5% water, 94% ethanol/6% water, 93% ethanol/7% water or 92% ethanol/8% water.

A typical amount of the water/ethanol mixture is about 150 ml to 200 ml of water/ethanol per gram of Vilazodone hydrochloride, preferably about 170 ml to 200 ml of water/ethanol per gram of Vilazodone hydrochloride.

The suspension can then be heated, for example to a temperature of about 70 to 80° C., such as, in the case of 96% ethanol, up to the boiling point of 96% ethanol, to facilitate the preparation of a solution. The presence of some water in the dissolution step of Vilazodone hydrochloride facilitates solubilization. As an example, 1 g of Vilazodone hydrochloride may be dissolved in about 170 to 200 ml of ethanol containing about 7 to 9 ml of water (v/v). The obtained solution then can be filtered, slowly cooled to about 20° C. to 30° C. and then seed crystals of Vilazodone hydrochloride monoethanol monohydrate solvate can be added.

The seeds of Vilazodone hydrochloride monoethanol monohydrate solvate can be obtained by suspending the known form III of Vilazodone hydrochloride in 96% ethanol and stirring the suspension for an extended period of time at ambient temperature, such as described in example 1. The seeds can optionally be isolated from the suspension by filtration (suction).

The suspension which forms upon crystallization of Vilazodone hydrochloride monoethanol monohydrate solvate from the water/ethanol mixture can be stirred for several hours, e.g. for about 6 to 24 hours, for example at a low to ambient temperature. The yield may be increased by keeping the suspension at about 0 to 10° C. for a period of time sufficient to essentially complete crystallization, e.g. for 6 to 24 hours, preferably about 8 to 12 hours.

Optionally the solution or the suspension may be diluted, for example with ethanol or water/ethanol, e.g. 96% ethanol, for example by adding 0.5 to 2 volumes of ethanol or water/ethanol, relative to the volume used in the dissolution step.

Vilazodone hydrochloride monoethanol monohydrate solvate can then be isolated by appropriate means, such as by filtration or centrifugation, optionally washed with ethanol (96%) and can then be sucked dry, e.g. on a suction filter, e.g. under vacuo.

In a preferred example of the process for the production of vilazodone hydrochloride monoethanol monohydrate solvate, vilazodone hydrochloride can be suspended in 96% ethanol and heated to reflux. After most of the material has dissolved, the slightly yellow solution can be filtered using a syringe filter (0.2 μm Pall GHP Acrodisc 13 mm). To this hot filtrate ethanol can be added and heated to reflux. The boiling solution can be cooled to 25° C. and then a suspension of seed crystals can be added. The suspension thus obtained can be stirred at about 25° C. for 4 hours and then allowed to stand in the fridge (temperature about 4° C.) for about 12 hours.

The formed Vilazodone hydrochloride monoethanol monohydrate solvate can then be isolated by filtration, optionally washed with ethanol (96%) and sucked dry, e.g. on a suction filter under vacuo for e.g. for 15 minutes.

In another embodiment the invention relates to a process for the manufacture of Vilazodone form III comprising the step of
  i. converting Vilazodone hydrochloride monoethanol monohydrate solvate to form III of Vilazodone hydrochloride.

The process causing the conversion of the Vilazodonone hydrochloride monoethanol monohydrate solvate to vilazodone hydrochloride form III is not particularly limited. Without wishing to be bound by any theory, it is thought that desolvation of the Vilazodonone hydrochloride monoethanol monohydrate solvate causes a rearrangement of the crystal order to yield form III of vilazodone hydrochloride. Vilazodonone hydrochloride monoethanol monohydrate solvate can for example be converted to form III of Vilazodone hydrochloride by drying, such as in vacuo at about 10 to 20 mbar and at a temperature up to about 80° C. for a period which is sufficient for conversion, preferably at a temperature of about 40 to 60° C. for several hours, e.g. for about 4 to 24 hours.

In another embodiment the invention relates to a process for the manufacture of Vilazodone form III comprising the steps of
  (a) providing a solution of 5-4-[4-5-cyano-1H-indol-3-yl)butyl]piperazin-1yl)benzofuran-2-carboxamide hydrochloride (vilazodone hydrochloride) in a water-ethanol mixture,
  (b) precipitating Vilazodone hydrochloride monoethanol monohydrate solvate in the presence of seed crystals,
  (c) optionally diluting the suspension with ethanol or water/ethanol,
  (d) recovering Vilazodone hydrochloride monoethanol monohydrate solvate from the suspension,
  (e) drying Vilazodone hydrochloride monoethanol monohydrate solvate to yield form III of Vilazodone hydrochloride.

The individual steps of this process have already been described above.

The process for the preparation of Vilazodone hydrochloride form III is not limited to a laboratory process and can be scaled up for a manufacturing plant for multi-kilogram production of vilazodone hydrochloride form III.

It is an advantage that vilazodone hydrochloride monohydrate monoethanol solvate can be converted to form III of Vilazodone hydrochloride under mild conditions. For example, the conversion of the Vilazodonone hydrochloride monoethanol monohydrate solvate to form III of Vilazodone hydrochloride by drying in vacuo, e.g. at about 10 to 20 mbar at a temperature of preferably about 40 to 60° C. for several hours, e.g. for about 4 to 24 hours, helps to avoid chemical decomposition of vilazodone hydrochloride, while at the same time it is sufficient to efficiently remove residual solvent traces in the formed vilazodone hydrochloride form III.

It is a further advantage that vilazodone hydrochloride form III obtained by the conversion of the vilazodone hydrochloride monohydrate monoethanol solvate has a decreased level of residual solvents compared to the previously available vilazodone hydrochloride form III.

Residual solvent determination, such as explained below for the measurement of residual tetrahydrofurane content in Vilazodone hydrochloride form III of the present invention, can be measured by techniques known in art, e.g. such as gas chromatography.

Analysis can be performed on a gas chromatography equipment with a flame ionization detector (FID) and with Headspace sampler. The internal standard solution (ISS) can be prepared by adding 1-propanol to dimethyl sulfoxide (DMSO) to produce a solution of 1 mg/ml, and mixed well. A standard stock solution for a mixture of residual solvents such as methanol, ethanol, acetone, ethyl acetate, THF, pyridine and DMF can be prepared by adding standards of the above solvents in DMSO to produce a solution containing 1 mg/ml of each methanol, ethanol, acetone and ethyl acetate, 0.07 mg/ml tetrahydrofurane, 0.02 mg/ml pyridine and 0.09 mg/ml DMF.

To make a standard solution, 5 ml of the stock solution can be transferred to a 20 ml headspace vial. One ml ISS can be added, and diluted to 10 ml with DMSO. The vial is to be sealed after the addition.

Sample can be prepared as follows:

One gram of Vilazodone hydrochloride form III is to be weighed accurately and can be added into a 20 ml headspace vial. One ml ISS is to be added, then diluted to 10 ml and the vial is then to be sealed.

The spiked sample solution can be prepared by weighing 1 g of Vilazodone Hydrochloride form III into six headspace vials and 1 mL ISS of is to be added to each vial. Five ml stock solution can be transferred into each vial and diluted with DMSO to 10 ml. The vials are to be sealed.

Conditions:
Column: DB 624
Carrier: Nitrogen constant flow mode, 4.5 mL/min
Oven:
  40° C. for 8 min
  40 to 200° C. at 45° C./min
  200° C. for 3 min
Sample loop 1 mL
Temperature Oven 80° C., Loop 110° C. transfer line 130° C.
Vial equilibrium time: 30 min
Inlet 200° C. split ratio 3:1
Detector FID at 250° C.
Sampler: Headspace sampler
Instrument: Gas Chromatography The organic volatile impurity (OVI) in the obtained vilazodone hydrochloride form III thus analyzed was detected to be less than 300 ppm, preferably less than 100 ppm, more preferably less than 50 ppm. Vilazodone hydrochloride form III is essentially free of THF. Residual ICH class 2 solvents are not detectable.

Thus, in a further embodiment, the present invention relates to vilazodone hydrochloride crystal form III wherein at most 300 ppm of ICH class 2 solvent are present. Preferably at most 200 ppm, such as at most 150 ppm, such as at most 100 ppm, such as at most 90 ppm, at most 80 ppm, at most 70 ppm, at most 60 ppm, at most 50 ppm, at most 40 ppm, at most 30 ppm, at most 20 ppm and most preferably at most 10 ppm residual ICH class 2 solvents are present, in particular when measured according to the above-described residual solvent method. The present invention also relates to vilazodone hydrochloride form III which is essentially free from ICH class 2 solvents, in particular essentially free from tetrahydrofurane. Preferably, the obtained vilazodone hydrochloride form III of the present invention has an overall organic volatile impurity content of up to 300 ppm, such as up to 100 ppm, for example 50 ppm, and being essentially free from ICH class 2 solvents, such as tetrahydrofurane.

In a further embodiment the present invention relates to vilazodone hydrochloride form III obtainable by the processes of the present invention, such as the process of example 3.

The present invention also relates to a pharmaceutical composition comprising Vilazodone hydrochloride form III as an active pharmaceutical ingredient, and a pharmaceutically acceptable excipient, and wherein at most 300 ppm of an ICH class 2 solvent are present. Preferably at most 200 ppm, such as at most 150 ppm, such as at most 100 ppm, such as at most 90 ppm, at most 80 ppm, at most 70 ppm, at most 60 ppm, at most 50 ppm, at most 40 ppm, at most 30 ppm, at most 20 ppm, for example at most 10 ppm residual ICH class 2 solvents are present in the pharmaceutical composition of the invention. The present invention also relates to a pharmaceutical composition comprising vilazodone hydrochloride, such as vilazodone hydrochloride form III which is essentially free from ICH class 2 solvents, in particular which is essentially free from tetrahydrofurane.

Applying techniques known in the art may be carried out formulating crystal form III of Vilazodone hydrochloride into a dosage form in different strengths.

By way of an example, tablets may be prepared in strengths of 10 mg, 20 mg and 40 mg as immediate-release tablets. In addition to the active ingredient, the tablets may contain lactose monohydrate, microcrystalline cellulose, magnesium stearate, colloidal silicon dioxide, polyvinyl alcohol, titanium dioxide, polyethylene glycol, talc, FD&C Blue #1 (40 mg only), FD&C Yellow #6 (20 mg only) and FD&C Red #40 (10 mg only).

The pharmaceutical compositions of Vilzodone hydrochloride form III are useful for treatment and prevention of depressive disorders, anxiety disorders, bipolar disorders, mania, dementia, substance-related disorders, sexual dysfunctions, eating disorders, obesity, fibromyalgia, sleeping disorders, psychiatric disorders, cerebral infarct, tension, for the therapy of side effects in the treatment of hypertension, cerebral disorders, chronic pain, acromegaly, hypogonadism, secondary amenorrhea, premenstrual syndrome and undesired puerperal lactation, in particular wherein the patient to be treated is allergic to ICH class 2 solvents, such as tetrahydrofurane.

In a further embodiment the present invention also relates to the use of Vilazodone hydrochloride monoethanol monohydrate solvate for the production of Vilazodone hydrochloride crystalline form III, in particular vilazodone hydrochloride form III wherein at most 300 ppm of organic volatile impurities, such as an ICH class 2 solvent, are present. Preferably at most 200 ppm, such as at most 150 ppm, such as at most 100 ppm, such as at most 90 ppm, at most 80 ppm, at most 70 ppm, at most 60 ppm, at most 50 ppm, at most 40 ppm, at most 30 ppm, at most 20 ppm, for example at most 10 ppm residual organic volatile impurities, such as residual ICH class 2 solvents, are present, such as in vilazodone hydrochloride form III which is essentially free from ICH class 2 solvents, in particular which is essentially free from tetrahydrofurane.

The following examples describe the present invention in detail, but are not to be construed to be in any way limiting for the present invention.

EXAMPLES

Example 1

Preparation of Seeds of Vilazodone Hydrochloride Monoethanol Monohydrate Solvate 50 mg of Vilazodone hydrochloride form III prepared according to example 11 of WO 02/102749 were stirred in 2 ml 96% ethanol/water (ratio: 4:1 v/v) for about 20 hours. A suspension is obtained. The crystals were then isolated by filtration followed by drying by suction for about 15 min. The crystals were then subjected to single crystal analysis.

Example 2

Preparation of Vilazodone Hydrochloride Monoethanol Monohydrate Solvate 0.500 g (10.5 mmol) Vilazodone hydrochloride form IV (described on page 18 of WO 02/102794) were suspended in 80 ml ethanol (96%) and heated to reflux. After 10 minutes most of the material has dissolved and the slightly yellow solution is filtered hot using a syringe filter (0.2 µm Pall GHP Acrodisc 13 mm). To this hot filtrate 16 ml ethanol (96%) was added and the solution again heated to reflux conditions for 1 minute. The boiling solution was cooled to 25° C. and seeded with 250 µl of the suspension prepared according to example 1. The suspension was stirred at about 25° C. for 4 hours and was then allowed to stand in the fridge (temperature about 4° C.) for about 12 hours. The crystals were then isolated by suction filtration (filter funnel porosity 3), washed two times with mother liquor and left at the water vacuum pump for 15 minutes.

Yield: 323.5 mg

Example 3

Preparation of Vilazodone Hydrochloride Form III 0300 mg Vilazodone hydrochloride monoethanol monohydrate solvate was dried in a vacuum drying oven for four hours (50° C., 27 mbar).

Yield: 258.2 mg

The sample was analyzed by PXRD as described above, 2 Theta values and relative intensities are shown in table 2.

Example 4

Pharmaceutical composition using Vilazodone hydrochloride form III produced by the sequence of examples 1, 2 and 3.

| Composition | 10 mg mg/unit | 20 mg mg/unit | 40 mg mg/unit |
|---|---|---|---|
| Vilazodone hydrochloride form III | 10.00 | 20.00 | 40.00 |
| Lactose | 40.00 | 80.00 | 160.00 |
| Microcrystalline cellulose | 40.10 | 40.20 | 80.40 |
| Magnesium stearate | 0.10 | 00.20 | 00.40 |
| Colloidal silicon oil | 1.00 | 02.00 | 04.00 |
| Titanium dioxide | 2.00 | 04.00 | 08.00 |
| Polyvinyl alcohol | 1.00 | 02.00 | 04.00 |
| Polyethylene glycol | 1.00 | 02.00 | 04.00 |
| Talc | 7.80 | 15.60 | 11.20 |

TABLE 2

PXRD of Vilazodone hydrochloride form III:
2 Theta values and relative intensities

| No. | Pos. [°2Th.] | Rel. Int. [%] |
|---|---|---|
| 1 | 5.8 | 65.7 |
| 2 | 8.4 | 4.39 |
| 3 | 9.4 | 15.34 |
| 4 | 11.0 | 30.41 |
| 5 | 11.8 | 19.6 |
| 6 | 13.1 | 10.42 |
| 7 | 13.9 | 25.71 |
| 8 | 15.1 | 41.36 |
| 9 | 16.9 | 55.13 |
| 10 | 17.5 | 30.36 |
| 11 | 18.0 | 32.72 |
| 12 | 18.8 | 6.4 |
| 13 | 20.0 | 7.05 |
| 14 | 21.0 | 48.24 |
| 15 | 22.2 | 52.73 |
| 16 | 23.9 | 17.34 |
| 17 | 24.6 | 13.27 |
| 18 | 25.4 | 100 |
| 19 | 26.5 | 8.73 |
| 20 | 27.1 | 10.69 |
| 21 | 28.1 | 15.16 |
| 22 | 29.2 | 5.54 |
| 23 | 30.8 | 6.3 |
| 24 | 32.4 | 6.46 |
| 25 | 34.3 | 2.87 |
| 26 | 36.6 | 3.13 |

The invention claimed is:

1. A process for the preparation of form III of Vilazodone hydrochloride comprising converting Vilazodone hydrochloride monoethanol monohydrate solvate to form III of Vilazodone hydrochloride by desolvation of the monohydrate solvate.

2. The process according to claim 1, wherein Vilazodone hydrochloride monoethanol monohydrate solvate is converted to form III of Vilazodone hydrochloride by drying at 50° C.

3. A process for the preparation of form III of Vilazodone hydrochloride comprising the steps of:

(a) providing a solution of vilazodone hydrochloride in ethanol or in a water/ethanol mixture;

(b) precipitating vilazodone hydrochloride monoethanol monohydrate solvate in the presence of seeds;

(c) optionally diluting the suspension with ethanol;

(d) recovering vilazodone hydrochloride monoethanol monohydrate solvate from the suspension; and (e) drying vilazodone hydrochloride monoethanol monohydrate solvate to yield form III of vilazodone hydrochloride.

4. The process according to claim 3, wherein the ethanol/water mixture contains from 4% (v/v) to 8% (v/v) of $H_2O$.

5. The process according to claim 3, wherein at most 300 ppm of ICH class 2 solvent is present in the vilazodone hydrochloride form III formed in step (e).

6. The process according to claim 3, wherein at most 100 ppm of ICH class 2 solvent is present in the vilazodone hydrochloride form III formed in step (e).

7. The process according to claim 3, wherein at most 10 ppm of ICH class 2 solvent is present in the vilazodone hydrochloride form III formed in step (e).

8. The process according to claim 3, wherein the vilazodone hydrochloride form III formed in step (e) is free from ICH class 2 solvents.

* * * * *